Figure 1:
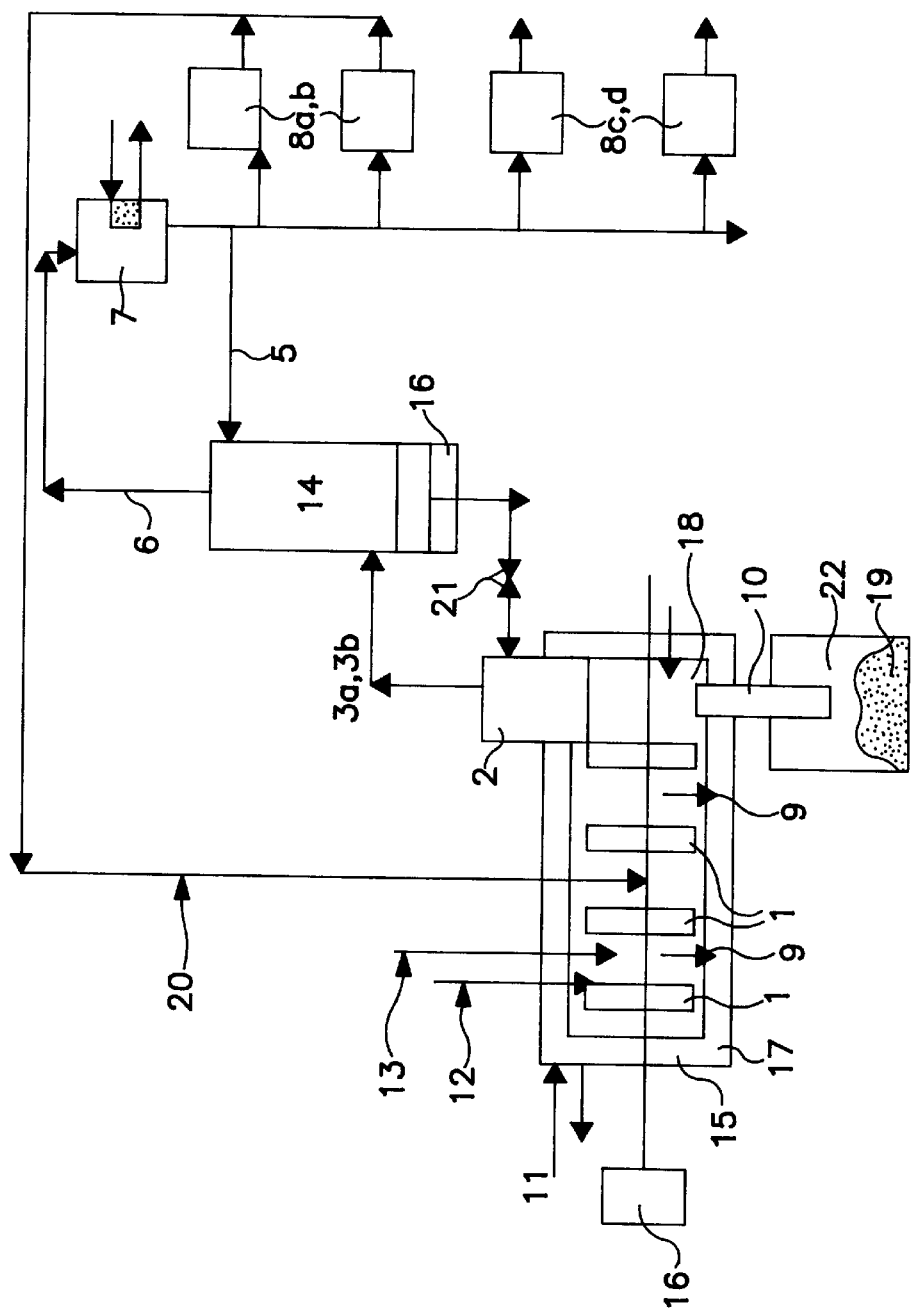

United States Patent [19]
Giebeler

[11] Patent Number: 5,808,159
[45] Date of Patent: Sep. 15, 1998

[54] PROCESS AND DEVICE FOR RECOVERING AMINES AND USE OF RESIDUES OBTAINABLE THEREBY

[75] Inventor: Eberhard Giebeler, Schriesheim, Germany

[73] Assignee: TRG Technologie Und Recyclingservice GmbH, Germany

[21] Appl. No.: 663,198
[22] PCT Filed: May 3, 1995
[86] PCT No.: PCT/DE95/00595
§ 371 Date: Jun. 10, 1996
§ 102(e) Date: Jun. 10, 1996
[87] PCT Pub. No.: WO95/31430
PCT Pub. Date: Nov. 23, 1995

[30] Foreign Application Priority Data

May 11, 1994 [DE] Germany ............... 44 16 571.4

[51] Int. Cl.$^6$ ............... B01D 3/00; C07C 209/00
[52] U.S. Cl. ............... 497/197; 202/200
[58] Field of Search ............... 564/497; 203/12, 203/13, 14, 36, 37, 71, 73, 80; 202/200, 235, 175; 159/6.1

[56] References Cited

U.S. PATENT DOCUMENTS

| | | | |
|---|---|---|---|
| 3,741,272 | 6/1973 | Ullrich et al. | 159/2 E |
| 4,472,246 | 9/1984 | Stamerjohn et al. | 203/37 |
| 4,919,911 | 4/1990 | Shirota et al. | 423/499 |

*Primary Examiner*—S. Mark Clardy
*Assistant Examiner*—Barbara Badio
*Attorney, Agent, or Firm*—Bierman, Muserlian and Lucas

[57] ABSTRACT

The invention relates to a process for recovering amines from acid amine salt solutions by the addition of bases and evaporating the solution at a pH of 11 to 13 in a kneading drier until a useful solid is obtained as the distillation residue and a device for separating sludges and suspensions into a solid and a plurality of liquid fractions separated according to their boiling point. The low-water-content amine phase separated out by distillation is dehydrated with calcium oxide or potassium hydroxide and then separated into pure amine fractions by rectification. The process described makes it possible to utilise all the secondary flows and completely recycle the amines and the absorption medium (sulphuric acid). The flows for the recycling process are amine-charged washing acids from absorbers obtained from the cleaning of amine-containing exhaust gases, produced for instance in the cold box process for hardening core sand in foundries.

11 Claims, 2 Drawing Sheets

PROCESS AND DEVICE FOR RECOVERING AMINES AND USE OF RESIDUES OBTAINABLE THEREBY

This application is a 371 of PCT/DE 95/00595 filed May 3, 1995.

DESCRIPTION

Amines are used in numerous processes as reaction partners, solvents and catalysts. Examples are the production of quaternary ammonium compounds and the catalytic hardening of polyolisocycanate-binder systems (e.g. cold box process for hardening core sand in foundries).

Because of the offensive smell and the low toxicity threshold of the amines an aftertreatment of the exhaust air is necessary at those processes in order to dispose the amines safely or to recover them.

A common gas purifying process is the thermal post-combustion, where the amines are burnt. In the post-combustions it is possible by a complex reaction procedure and the addition of ammonia to control the nitrogen oxide emission. In small plants with discontinuous production as for example the cold box core producing plants in foundries this process is generally not to be controlled effectively. In any case it's also a disadvantage that a valuable chemical substance is burnt which is additionally present in an unfavourably high dilution for combustion.

Another very common process is the chemical absorption of the amines contained in the exhaust air into mineral acids. As absorbers there are used e.g. spraying absorbers or packed columns with reverse flow procedure. In a 15–40% sulphuric acid amine charges in the range of 10–30% are reached in practice depending on the amine and acid concentrations. It is essential to work in a pH-range below pH 3 to avoid amine emissions. The advantage of this process is that the amines are concentrated in the acid simply and safely with regard to process technology and that gaseous emissions can be avoided.

Instead of sulphuric acid also other acids e.g. phosphoric acids can be used. The cheap sulphuric acid is, however, preferred.

By the absorption the problem of disposal has been transferred from the exhaust air primarily to the acid charged with amine. The problem resulting from that is the disposal or usage of the saturated scrub liquors. In practice the following ways of disposal for the exhausted absorber liquid are gone:

1. Dilution with the sewage after neutralisation and decomposition of the amines in a biological sewage treatment plant.

Therewith the amines are lost without using them. The high salt freight means a contribution to salting up the lakes and rivers and in the case of the usual application of sulphuric acid as absorption liquid means a significant source of corrosion for drains made of concrete. Apart from that after the necessary neutralisation of the sewage a part of the amines escapes as gaseous emission.

2. Combustion of the amine sulphate solutions in cracking ovens.

Here the amines are burnt and the sulphates are turned into sulphur oxides. In plants especially designed for this purpose the sulphur dioxide can be utilised e.g. for the production of sulphuric acid. This process is complex and means a loss of the amines which are valuable chemicals.

3. Recovering amines from the scrub liquors.

In the patent specification DE 31 04 343 Al (Arasin) an amine recycling process is described which is based on phosphoric acid as absorption liquid. The charged amine phosphate solution is neutralised in the recycling plant with calcium oxide or calcium hydroxide. By stirring and warming up until max. 105° C. the amines are set free in a stirring boiler and subsequently condensed and distilled. For dehydrating the amine/water-azeotropes molecular sieves are suggested.

The patent specification also deals with the reprocessing of the residue consisting of a suspension of calcium hydroxide and calcium phosphate remaining in the stirring boiler. It is neutralised with phosphoric acid. Then you let the solid deposit and you filter the sludge deposited. Previous experience has shown that the watery solution on top is not completely deaminated; this is the reason why the reuse of this solution is described in the deamination stage.

For drying the—as the solution on top—also still amine-containing filter cake well-known drying types as fluid bed driers and hurdle driers are named. The dried filter cake consists of calcium phosphate, a usable raw material. Due to the great number of processing stages and the usage of phosphoric acid the process is expensive and complex. In the process description the essential question, how amine emissions during the multi-stage handling of the solid are avoided, remains without an answer. This is—besides the high expenditure for the process—a reason for this process not being used in practice. Apart from that no practicable way for the dehydration of the amine/water azeotropes is shown, especially the kind and the effect of the mol sieve and its desorption remain open.

The U.S. Pat. No. 4.472.246 (Ashland Oil 1984) describes a process for recovering amines used in practice. Thereby the originally acid scrub liquor is mixed with inorganic bases from the series of alkali or alkaline earth metal hydroxides and warmed up above the boiling point of the amines. While the process seems easy-to-apply for amines not forming azeotropes with water, the described separation of amine/water-azeotropes by phase breaks and redistillations is very complex and presumably hardly to be carried through in practice. In the patent claims and in the example the expressive limitation to amines not forming azeotropes with water, as dimethylethylamine, is striking.

The patent of Ashland Oil described above does not deal with the usage or disposal of the by-product, the salt residue resp. the salt solution in the distillation pot. This problem is not solved by removing the amine-free salt solution from the distillation pot and is the weak point of the process described above.

The process described in an example in the patent of Ashland Oil and common in practice today uses a 50% caustic soda as base. Besides the favourable price and the good availability caustic soda has got the essential advantage that the solubility of the sodium sulphate formed as reaction product with amine sulphate is good at high temperatures, e.g. compared to potassium sulphate or calcium sulphate.

Solubilities of salts in water at 100° C.:
Sodium sulphate: 43 g/100 ml of water
Potassium sulphate: 24 g/100 ml of water
Calcium sulphate: 0,16 g/100 ml of water This high solubility of sodium sulphate has got the advantage that concentration deposits in the distillation pot can be avoided. The danger of incrustation of the heat exchanger surfaces with sodium sulphate is, however, given to a certain extent.

In the case of using caustic potash it would be necessary to work with nearly the double dilution with water as in the case of caustic soda, in order to control concentration deposits. In the case of using lime as cheapest base a deposit of calcium sulphate would develop in any case. In this sludge amine sulphate and amines are included and a complete separation of the amines by distillation would also be difficult because of the bad heat transfer in the sludge or even impossible in usual distillation pots.

The use of calcium hydroxide for deaminating the amine sulphate solutions in the customary distillation plants, although included in the patent claims of Ashland Oil, is practically not to be carried through in practice for the reasons mentioned above and is therefore not used despite of lime products being the cheapest bases.

In practice the usage of caustic soda for recovering amines is the solution used for the reasons described above, although the subsequent disposal of the distillation residue, a mixture or caustic soda, water and sodium sulphate, in view of increasing ecological requirements is a serious problem.

Altogether the lacking or insufficient usability of these residues still contaminated with process-typical products after the amine separation is the essential weak point of the amine recycling process. In the case of the cold box process (hardening of sand binding agents in foundries on the basis of polyol/isocyanate with amine catalysts) e.g. finest quartz particles and organic solvents are carried into the acid scrub liquor. These contaminations contribute to the fact that the disposal of the salt-containing residues is a problem. The quantity of the residues to be disposed is nearly as big as the quantity of amine sulphates used initially, i.e. no quantitative relief at the disposal of residues takes place by the recycling process.

The following ways of disposal for the distillation residue suggest themselves:

1. Neutralisation of the alkaline residue and crystallisation of the sodium sulphate. This process is complex and doesn't generally lead to a usable sodium sulphate because of contaminations of the sodium sulphate caused by the process. Sodium sulphate as an unwanted by-product represents a well-known problem of utilisation so that the deposition of the sodium sulphate is a solution of the problem. But because of the considerable smell molestation of the generally adherent minimum quantities of amine in practice this way is without significance.

2. Dosing of the hot sodium sulphate solution from isolated and heatable tanks into the sewage system of the sewage treatment plant. This is the current practice. Again the unwanted consequence is a salting-up effect of the sewage and the danger of concrete corrosion by the sulphate ions.

To sum up it can be said that the process described in the patent specification of Ashland Oil is only useful and can only be handled if the distillation residue can be led into the sewage without the danger of concrete corrosion; and the patent specification is based on this situation apparently. This is, however, not always allowed and admissible for reasons of protection against corrosion and protection of lakes and rivers. A further disadvantage of the process described by Ashland Oil is the practical limitation to amines not forming azeotropes with water. Amines forming azeotropes with water, as e.g. triethylamine with 10% of water in the azeotrope, have got a considerable significance on the market.

Therefore it is the main task of the invention to find a simple process for the recycling of all amines especially all aliphatic amines providing a possibility of utilisation for all by-products and avoiding the problems connected with the distillation and the handling of sludges and supersaturated salt solutions leading to a solid as distillation residue easily to be handled.

The process of the invention for recovering amines from acid amine scrub liquors comprising neutralizing an acid amine scrub mixture with a stoichiometric excess of a base, evaporating and distilling the liquid fraction of the resulting mixture in a kneading evaporator to obtain a solid distillation residue and a condensed amine/water phase and recovering amine from the amine/water phase. A novel kneading evaporator of invention is provided with indirect heating and kneading gaps of 1.5 to 10 mm, the outlet being provided with a heat isolated dome, the dome being connected in series to a rectification column connected to a condenser, which can be advantageously used not only for the amine recycling and the dehydration of amine/water-azeotropes but also generally for the separation of sludges into a solid and several fractions of vaporisable liquid phase components.

Surprisingly enough it has been found that especially a sludge produced from calcium oxide or calcium hydroxide and amine sulphate solution can be handled and completely deaminated if the neutralisation with subsequent deamination and thermal drying of the distillation residue is carried through in a special kneading drier, whereby the calcium oxide or calcium hydroxide is used in a stoichiometric excess to the sulphate content of the scrub liquor. For economical reasons usually the 1.5 fold of the stoichiometric excess will not be exceeded. In practice the lower limit is a stoichiometric excess of 5 to 15%. Burnt or slaked lime can also partially be substituted for neutralisation by calcium carbonate. It is a special advantage of the kneading drier and especially of the device described in claim 10 that therewith a simple process for the dehydration of amine/water-azeotropes and for the preparation of these amines in a pure condition is also possible in the same plant.

The types of the kneading drier [(15), FIG. 1] preferentially used besides a wall heating (17) also have kneading and mixing devices (1) heated with thermal oil or water vapour (11) attached to driving axle (22), the design of which makes possible an intense surface renewal and mixing of the tough stage developing in the final stage of drying. The feature of these kneading driers are narrow gaps between moving and static kneading organs in the range of 1,5–7 mm. For improving the breaking up process and the production of a small average grain size rotating cutting knives (18) can be installed in the zones not brushed over by the kneading organs. Those driers are self-cleaning; temporary incrustations at the heating surfaces are decomposed again and again. As an example for a kneading drier especially the kneading driers of the product line Discotherm of the company List AG, Switzerland are to be mentioned, which are able to break very tough stages in the final stage of drying. The driving motor (16*a*) is designed heavy duty for the corresponding performance.

Instead of the indirect heating a direct heating e.g. with water vapour is also possible, but not preferred because of the increase of the quantity of water in the system therewith connected.

The drying process takes place by evaporating of the amine (3*a*) set free from the reaction of the amine solution (13) e.g. with the calcium oxide (12) and nearly the whole water quantity (3*b*), apart from a remaining water content in the range of 0,5% to approx. 20%. A water content essentially higher doesn't lead to pourable solids, but is basically also possible, if the pourable consistency is not demanded. For the final drying takes places at normal pressure or at a slight excess pressure preferentially at temperatures between 120° and 170° C. or at vacuum drying in the range of 100°–150° in this final stage besides residual quantities of amines also higher-boiling organic contaminations as e.g. hydrocarbons, which are used as solvents in the cold box process, together with the water vapour are practically completely separated from the inorganic residue.

According to this process there can be obtained in only one working step besides the amine a completely deaminated pourable distillation residue (19), which is discharged through an appropriate sluice e.g. a cellular wheel sluice (10) into a receiver (22). The grain size distribution can be influenced and controlled by the adjustment of the drying grade, the dimensioning of the mixing devices, the rotational speed of the kneader, and the temperature programme.

In the case of using lime and lime products as slaked or burnt lime as a base a utilisation of the solid residue at the cement production is given without a preliminary neutralisation of the residue, because the contents, calcium sulphate and calcium oxide or calcium hydroxide, as well as quartz are raw materials for the production of cement.

If the deamination is consciously carried through at a stoichiometric excess of calcium as low as possible a relatively pure gypsum with a low excess of calcium oxide is obtained as residue. During drying at temperatures above 120° the gypsum modification of the beta-hemihydrate is preferentially formed at normal pressure, which can also be directly used as building material in the gypsum industry. If after the deamination of the gypsum sludge the drying is preferentially carried through at an excess pressure of 3–5 bar at temperatures up to 160° on these hydrothermal conditions, as generally known, preferentially the modification of the alpha-hemihydrate is obtained, which is used as gypsum building material with special flow characteristics in high-quality applications. It may be necessary to reduce the applied excess of calcium by the addition of sulphuric acid in order to produce a gypsum as pure as possible, which is necessary for crystallisation. The advantage of the production of this high-quality gypsum modification during the process of deamination is that the kneading drier makes possible this variant without further installations and essential costs. As an alternative to the production of the hemihydrates it is also possible to carry through the residual dehydration at temperatures below 50° C. in the vacuum or by an air flow for the specific production of gypsum as dihydrate. In this case the exhaust air is led into an amine washing device for washing out residual amine quantities. It depends on the respective market conditions, which gypsum modification is to be preferred.

In another variant of the process also possible caustic potash solution instead of calcium oxide is used for the neutralisation. The solid residue potassium sulphate or potassium phosphate obtained, as described above, in only one plant with discontinuous distillation/drying can be used as fertiliser constituent after neutralisation.

If other bases than lime or potassium hydroxide are used, the advantage of a concentrated pourable residue is also reached, but there are no favourable possibilities of using this solid.

The economically preferred variant is the use of calcium oxide or calcium hydroxide as base and the utilisation of the gypsum in the gypsum industry. Besides the low price it is an advantage of the calcium oxide that the hydration and neutralisation are very exothermic and this heat of reaction can be utilised for the distillation. This exothermy can on the other hand be reduced by adding calcium carbonate as base.

EXAMPLE 1

In a 7-1-kneading drier with heated kneading discs (type and manufacturer: List AG DTB Batch) and a heating surface of 0,3 $m^2$ 3000 g of calcium hydroxide (slaked lime) are measured out. Then at room temperature and normal pressure 5566 g of an amine sulphate solution with the composition of 18% sulphuric acid 70% water 12% amine (mixture of dimethylethylamine DMEA (84%), dimethylisopropylamine DMIPA (6%) and triethylamine TEA (8%) were added.

The pH-value of the obtained suspension of lime and calcium sulphate was 12. The heat of reaction led to a measurable increase in temperature from 24° C. to 27° C. The thermal oil temperature for the indirect heating of the drier was adjusted to 100° C. From 55° C. in the suspension an obvious evaporation and condensation of the amines was realized at normal temperature. 700 ml of organic phase are evaporated at a temperature up to 77° C. in the distillation pot (temperature of the suspension in the kneading drier). The increase of the thermal oil temperature to 150° C., then to 200° C. led to a rapid evaporation of the other amines and of water.

Altogether 1030 ml as amine fraction (boiling point<100° C.), then 1400 ml of a watery phase with slight amine smell, then 3400 ml of amine-free water were distilled off.

At a normal pressure water was distilled off up to a temperature of 170° C. in the distillation pot resp. in the kneading drier. 2 h after starting the experiment the discontinuous distillation/drying was terminated.

| Mass balance | Input: | 8566 g | Products: | Solid: | 2715 g |
|---|---|---|---|---|---|
| | | | | Water | 4800 G |
| | | | | Amine | 664 g |
| | Losses: | 351 g | | | |

The filling degree of the kneader was measured with 45% at the final stage of drying at a rotational speed of 30 rotations/min. The solid obtained had a wide grain size distribution in the range of 0–5 mm and a low dust tendency.

Analytical composition:

Solid: Calcium: 40%

Sulphate: 39%

Annealing residue: 92% (rest: hydrate water)

Amine: not detectable

Amine fraction 0–900 ml: 82% DMEA 5% DMIPA 8% TEA 4,6% water DMEA=dimethylethylamine; DMIPA=dimethylisopropylamin; TEA=triethylamine Water fraction 1400–4800 ml: TOC 1600 mg/l (TOC= total organic carbon/content of organic carbon); caused by finest carbon particles.

The water fraction with TOC 1600 mg/l is sewage appropriate for the sewage treatment plant. This water can also be used as addition to the scrub liquor in the amine washer. The water fraction containing more amine (0–1400 ml; beginning with boiling temperature 100° C.) is added to a further reaction formulation for the purpose of a better amine recovery or is led back to the amine washer as compensation for evaporated water. Instead of slaked lime in example 1 the addition of other commercial lime being appropriate for neutralisation, as lime milk or burnt lime would be possible.

Because no rectification with the objective to obtain fractions as pure as possible was carried through, but, as in usual kneading driers exclusively possible, a simple evaporation, the water content of the amine fraction was higher than corresponding to amine/water azeotropes. The water content can, however, be further reduced by a direct coupling of a kneading evaporator (15) incl. heat isolated dome containing a dust filter (2) and with a rectification column as shown in FIG. 1. In this case in a discontinuous procedure the three amine fractions one after the other can be separated in a high purity and isolated in tanks (8a–8c) after condensation in the condenser (7). While in the case of the dimethylisopropylamine and triethylamine fraction a subsequent dehydration is necessary because of the high water content of 4% resp. 10% of the azeotropes, the water content of the dimethylethylamine fraction can be adjusted to below 0.3% and therewith very specific via the number of exchange plates of the column (14) and the relation of reverse flow (5) and the product quantity led into the tanks (8). The residue (16b) collecting in the column (14) is preferentially led back into the kneading drier via a control valve (21). For the expert this separation of amines described is an easy separation task.

The coupling of kneading evaporator and rectification column is a device simply to be realized, which is put together from generally known components. Because this combination is new and applicable also for numerous other separation tasks, wherein a suspension of a solid in a liquid mixture is to be separated into the solid and the single components resp. the boiling fractions of the liquid mixture, this special device has been described as generally usable for separations of sludges into solids and several boiling fractions. Usually those suspensions are separated by carrying through a separation into the solid and the liquid mixture first e.g. by kneading evaporation or filtration and by subsequent separation of the liquid mixture in a usual rectification column. Especially in the case of viscous sludges with a solid part of >20% the proposed device can make possible special procedural advantages, because several aims can be realized in one plant. Examples for that are the separation of lacquer sludges into a solid and several fractions of the liquid phase and the amine drying described in the following example 2.

In the following example 2 a simple drying process with calcium oxide is described for the hydrous amine fraction; the calcium hydroxide formed thereby can be subsequently used as base for the neutralisation according to example 1 therewith not causing any disposal expenditure and contributing to the protection of the resources.

EXAMPLE 2

100 g of the amine fraction obtained in example 1 with 4.6% of water were mixed with 30 g of calcium oxide powder in a lock-up flask and allowed to stand overnight. The amine mixture on top was then examined again. The water content was reduced to 0,3%. Thus calcium oxide has got a drying effect on the amine/water-azeotropes sufficient for practical applications.

The dried amine mixture can be separated in a discontinuous or 2 continuous rectifications according to the state of art. The use of other drying agents as zeolithes (width of the sieve 4–10 Å ngström) or alkali hydroxide is also possible, but burnt lime is the preferred variant.

The coupling of kneading evaporator and rectification column according to claim 10 can be utilised for obtaining dimethylethylamine in one stage in a discontinuous procedure as lowest boiling fraction (boiling point 36° C. at normal pressure) in a purity of 99% and with a max. of 0,3% of water as a product which can be sold and is kept e.g. in tanks (8c) for intermediate storage. The amine/water-azeotropes obtained afterwards are collected separately e.g. in tanks (8a, b) and subsequently dried with burnt lime as described in example 2 and purified by rectification. For drying and rectification of the azeotropes they are preferentially dosed via the connecting line (20) into the kneading drier for chemical drying with burnt lime (12) and, after the dehydration, they are isolated in the rectification column (14) connected with. This procedure is a further example for the versatile combination of kneading drier and rectification column. In this case the deaminated lime residue is not transferred outward, but remains as base stock in the kneading drier for the purpose of neutralisation of the amine sulphate solution in the deamination stage.

Figure 2:
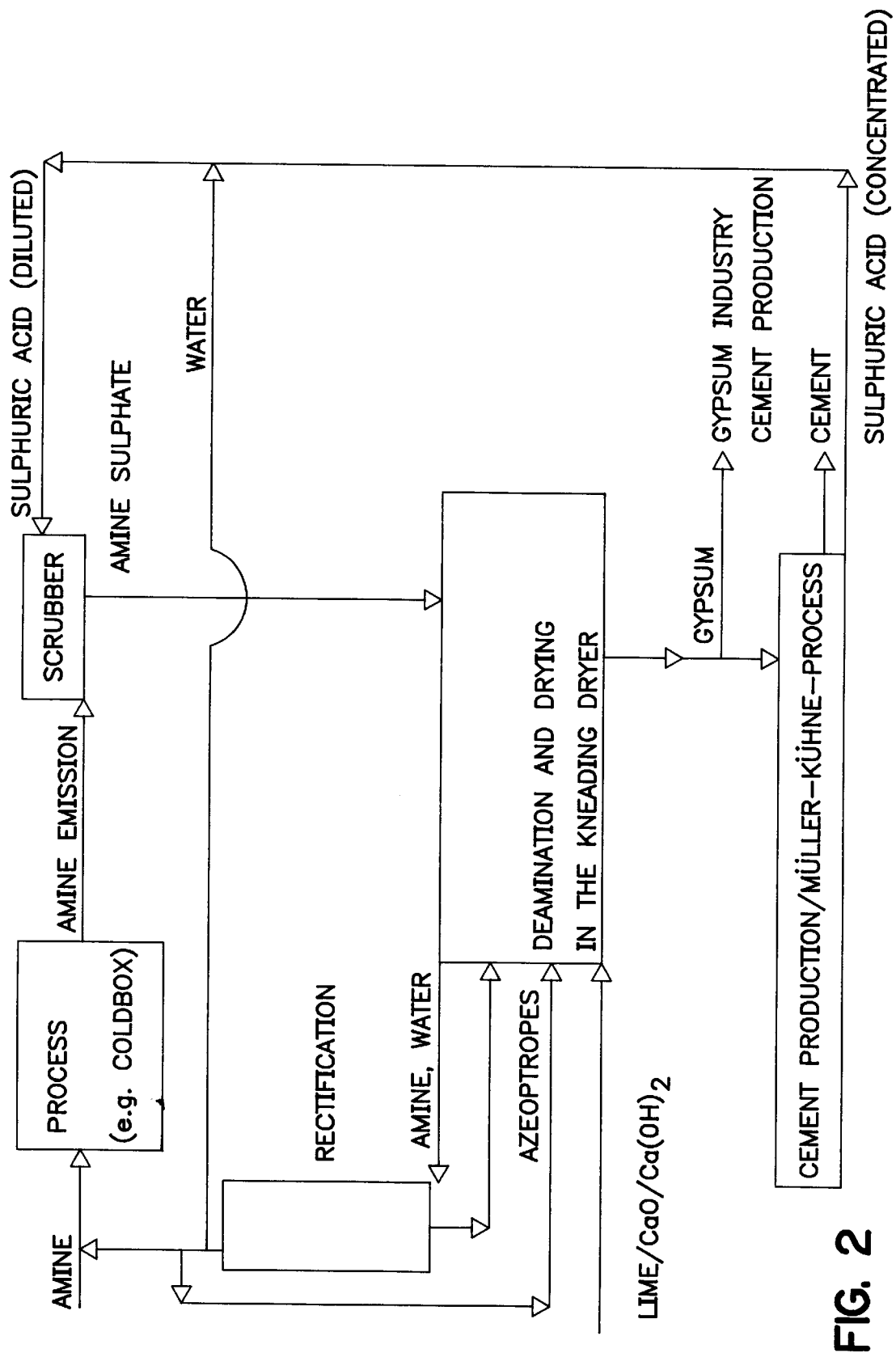

The advantages of the process combination described above 1. separation into solid, water phase and amine/water phase in the kneading drier
2. drying of the amine/water phase with calcium oxide
3. rectification of the dried amine phase are compared to the previous state of art:

avoiding of voluminous distillation residues
   avoiding of water addition during the neutralisation i.e. no further dilution of the amine sulphate, because concentration deposits don't have to be avoided any longer;
   the neutralising agent—e.g. burnt lime or anhydrous potassium hydroxide—is additionally utilised in its property as drying additive;
   the residue (calcium sulphate and slaked lime) of the distillation in the kneading drier described above is suitable for utilisation as cement raw material without previous neutralisation or as raw material to be used in the gypsum industry, e.g. in the form of alpha-hemihydrate.
   In a special variant the distillation residue, consisting of up to 90 of 95% of gypsum, can be transformed to cement and sulphuric acid in the Müller-Kühne-process. Therewith the closed loop materials economy is guaranteed for the sulphuric acid component as well. The flow chart FIG. 2 for this case shows a closed loop materials economy for amine and sulphuric acid, and the process additive lime is utilised in the form of gypsum for the production of cement via sulphate compounding.

The usual and preferential procedure is the discontinuous procedure, as described above. The volume of the kneading drier is mostly at 4–12 m³, but this range doesn't represent a technical restriction.

Instead of the batch operation also a continuous procedure can be carried through. In this case a separated collection of the single dehydrous amine fractions is not possible, unless several columns and kneaders are connected in series. In the case of large quantities of scrub liquors to be handled the continuous drying can be carried through either in a kneading drier with a large length/diameter relation (>5) and several zones separated from each other by retaining weirs (9) and axial temperature gradient or with several kneading driers connected in series. The choice between continuous and discontinuous operation is an economical optimisation task. An advantageous variant of the discontinuous operation is the semi-continuous operation, where it is distilled phasewise preferentially in 2 kneading driers connected in series. In the first drier for example the amine fractions are distilled off up to the boiling point of the water. Subsequently the distillation residue is pumped into the second drier, in which then the whole water fraction is separated. In the case of the second drier the rectification column is not necessary. With this procedure energy costs can be saved. The exhaust vapours or condensates of the second drier can be used for the heat energy supply of the first drier.

The working pressure during drying is preferentially in the range of 0,1–4 bar. In the final stage of drying the dehydration can be supported by producing a vacuum. If, however, the formation of an alpha-hemihydrate in the residue is wanted an excess pressure is chosen. In the initial stage of the reaction a slight excess pressure up to 2 bar is useful for improving the condensation and for better controlling of the reaction heat.

I claim:

1. A process for recovering amines from acid amine scrub liquors comprising neutralizing an acid amine scrub mixture with a stoichiometric excess of a base, evaporating and distilling the liquid fraction of the resulting mixture in a kneading evaporator to obtain a solid distillation residue and a condensed amine/water phase and recovering amine from the amine/water phase.

2. The process of claim 1 wherein the pressure in the kneading evaporator is 0.1 to 5 bar.

3. The process of claim 1 wherein the distilling and drying is effected in a series of kneading evaporators in a discontinuous reaction.

4. The process of claim 1 wherein the neutralization is effected at a temperature between the boiling point of the amine and effecting the distilling and drying step-wise to obtain one low water content amine fraction and a nearly amine free water fraction.

5. The process of claim 4 wherein the low water amine fraction is dried by contact with solid alkali metal hydroxide or calcium hydroxide to obtain a liquid amine phase which is rectified to recover the amine.

6. The process of claim 1 wherein the solid residue is a pourable solid containing less than 20% by weight of water.

7. The process of claim 1 wherein the base is calcium oxide or calcium hydroxide.

8. The process of claim 7 wherein the acid amine scrub liquor is an amine sulfate solution.

9. The process of claim 1 wherein the base is potassium hydroxide.

10. A kneading evaporator provided with indirect heating and kneading gaps of 1.5 to 10 mm, the outlet being provided with a heat isolated dome, the dome being connected in series to a rectification column connected to a condenser.

11. The kneading evaporator of claim 10 wherein the dome is equipped with a fine dust filter and the rectification column has 2 to 10 theoretical plates.

* * * * *